United States Patent
Franzmann et al.

(10) Patent No.: US 6,730,189 B1
(45) Date of Patent: May 4, 2004

(54) PROCESS FOR MANUFACTURING DISPOSABLE ABSORBENT ARTICLES, AND AN APPARATUS FOR PERFORMING THE PROCESS

(75) Inventors: Dirk Franzmann, Cologne (DE); Christoph Johann Schmitz, Euskirchen-Stotzheim (DE)

(73) Assignee: The Procter & Gamble Company, Cincinnati, OH (US)

( * ) Notice: Subject to any disclaimer, the term of this patent is extended or adjusted under 35 U.S.C. 154(b) by 57 days.

(21) Appl. No.: 09/979,494

(22) PCT Filed: Jun. 23, 2000

(86) PCT No.: PCT/US00/17489

§ 371 (c)(1),
(2), (4) Date: Jun. 7, 2002

(87) PCT Pub. No.: WO01/00122

PCT Pub. Date: Jan. 4, 2001

(30) Foreign Application Priority Data

Jun. 25, 1999 (EP) .............................................. 99112228

(51) Int. Cl.$^7$ .............................................. B32B 31/00
(52) U.S. Cl. ........................ 156/265; 156/270; 156/301; 156/302; 156/512; 156/519; 156/552; 156/559
(58) Field of Search ................................. 156/264, 265, 156/270, 303, 302, 300, 301, 299, 512, 518, 519, 520, 552, 560, 559

(56) References Cited

U.S. PATENT DOCUMENTS

| | | | |
|---|---|---|---|
| 5,034,007 A | | 7/1991 | Igaue et al. |
| 5,584,954 A | | 12/1996 | van der Klugt |
| 5,660,665 A | | 8/1997 | Jalonen |
| 5,683,533 A | * | 11/1997 | Keighley et al. ........... 156/204 |
| 5,705,013 A | * | 1/1998 | Nease et al. ................ 156/260 |
| 5,824,178 A | * | 10/1998 | Shingu et al. .............. 156/265 |

FOREIGN PATENT DOCUMENTS

| | | |
|---|---|---|
| EP | 0 396 050 B1 | 3/1995 |
| EP | 0 652 175 B1 | 5/1995 |
| WO | WO 96/21411 A1 | 7/1996 |

* cited by examiner

*Primary Examiner*—Linda Gray
(74) *Attorney, Agent, or Firm*—Michael S. Kolodesh; Jay A. Krebs; Ken K. Patel

(57) ABSTRACT

The invention provides a process and apparatus for the manufacture of disposable absorbent articles comprising the application of discrete web panels (40a, 40b) to a receiving web (1), wherein a plurality of first web panels (40a) and second web panels (40b) are cut from the same continuous web (40), and wherein the process comprises the steps of: cutting the continuous web (40) to form at least a first web panel (40a) and a second web panel (40b); rotating the second web panel (40); and applying the first web panel (40a) and the second web panel (40b) to the receiving web (1). The object of the invention is achieved by rotating the second web panel (40b) about an axis (A) perpendicular to the plane of the second web panel (40b)

10 Claims, 5 Drawing Sheets

PROCESS FOR MANUFACTURING DISPOSABLE ABSORBENT ARTICLES, AND AN APPARATUS FOR PERFORMING THE PROCESS

The invention relates to a process for manufacturing profiled disposable absorbent articles, and to an apparatus for performing the process. In a preferred embodiment the invention provides a process and apparatus for providing profiled side-panels, in particular elastic side-panels, without waste of the side-panel material. In particular, diapers or training pants may be made by the process of the invention having side "cut-outs" for better fit around the legs of the wearer, but the process may also be applied to feminine hygiene articles, adult incontinence articles, and other disposable absorbent articles.

Disposable absorbent articles have become very popular in the market place today. Many of these articles include features such as side-panels that provide a variety of functions including improved containment characteristics and better, more comfortable fit.

An overriding consideration in the construction of a disposable absorbent article is the cost of manufacturing the article, including the materials cost. The present invention provides methods for manufacturing side panels for absorbent articles with little or no wasted material. Thus, the side panels made by the process of the present invention can be provided at relatively lower cost than many of the side panels that are currently manufactured using techniques in which material is wasted. Processes which reduce or avoid material waste are disclosed in the following references.

U.S. Pat. No. 5,034,007, issued on Jul. 23, 1991, describes a method for cutting "nested ears" by making a periodic convex/concave cut lengthwise along a web. The two cut portions of the web are then separated and symmetrically arranged in the width direction with the straight edges on the inside and the convex/concave edge aligned on the outside. An alternative method of achieving the same result is disclosed in EP-A-0 396 050, published on Nov. 7, 1990. This discloses individually reversing all of the cut portions by turning them 180° about an axis lying in the plane of the web.

WO96/24319, published Aug. 15, 1996, discloses a method for manufacturing activated side-panels cutting in a "nested" pattern, and rotating all of the cut portions of the web through 180° about an axis lying in the plane of the web prior to attaching them to the diaper web (in particular this is illustrated in FIG. 7).

It is an object of the present invention to provide an alternative method of achieving the waste-saving advantages of "nested ears", and to provide an apparatus for use in the method.

The invention provides a process and apparatus for the manufacture of disposable absorbent articles comprising the application of discrete web panels to a receiving web, wherein a plurality of first web panels and second web panels are cut from the same continuous web, and wherein the process comprises the steps of:

cutting the continuous web to form at least a first web panel and a second web panel;

rotating the second web panel; and applying the first web panel and the second web panel to the receiving web.

SUMMARY OF THE INVENTION

The object of the invention is achieved by rotating the second web panel about an axis perpendicular to the plane of the second web panel.

DETAILED DESCRIPTION OF THE INVENTION

Figure 1:
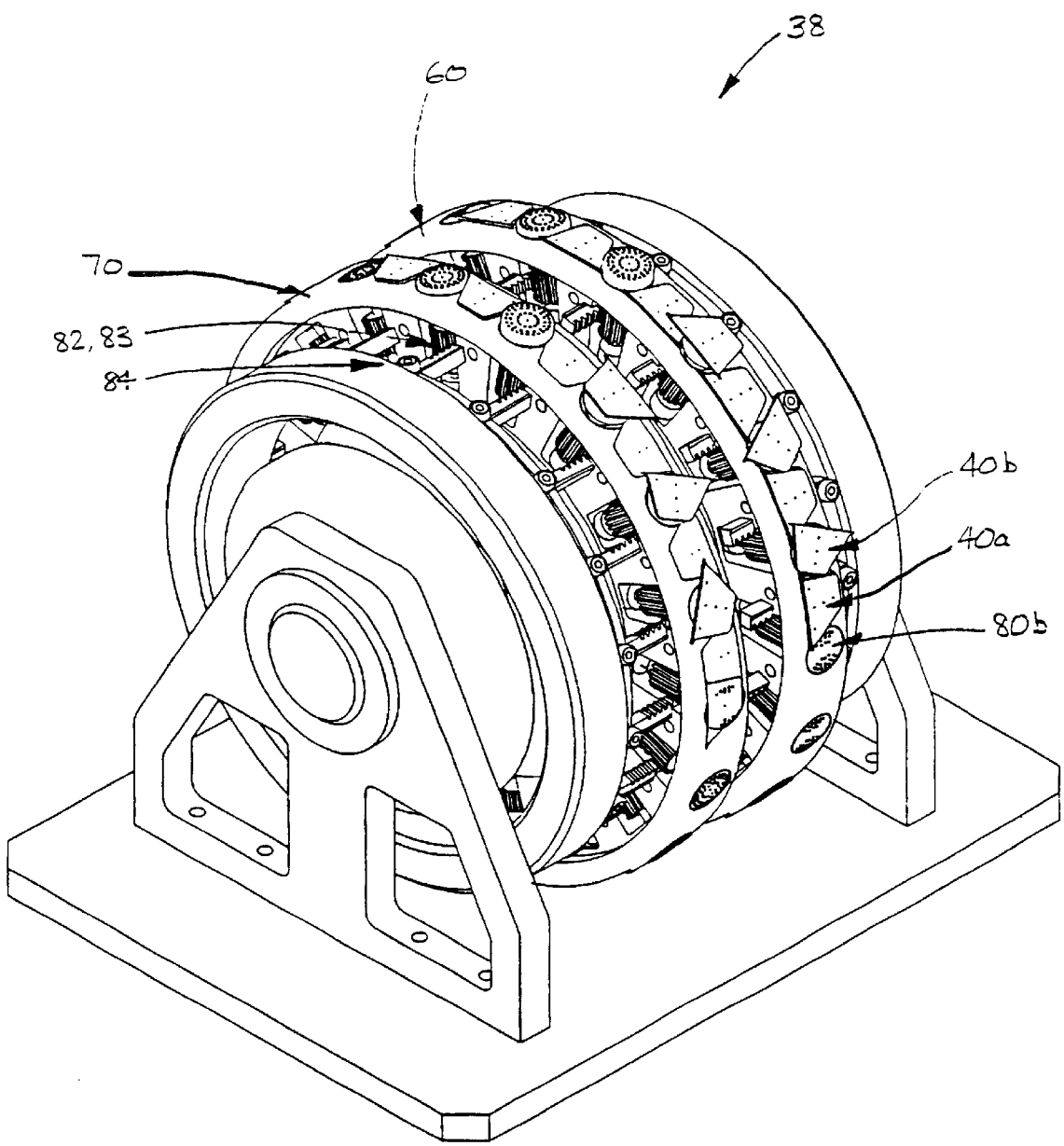
FIG. 1 shows a perspective view of an apparatus for use in the process of the present invention.

FIG. 1 shows a perspective view of an apparatus according to the present invention. The apparatus comprises two rotating drums 60, 70 which are essentially oriented symmetrically. The two drums 60, 70 apply discrete first and second web panels 40a, 40b to the left and right sides of the receiving web 1. In FIG. 1 a pair of incoming webs 40 are fed to the two sides of the apparatus and are cut in a nested pattern (see, for example, FIG. 4), and the discrete first and second web panels 40a, 40b of the incoming webs are held on vacuum shells 80a, 80b which are arranged around the circumference of each of the rotating drums 60, 70. The receiving web 1, the incoming webs 40, and the cutting roll 39 are not shown in FIG. 1 to simplify this illustration.

The drums 60, 70 are rotated about a main axis of the apparatus. In the embodiment illustrated in FIGS. 1 and 2, the main axis is oriented horizontally, but this main axis need not necessarily be horizontal in all cases. Most preferably the two drums 60, 70 are rotated synchronously, at the same speed.

In the embodiment shown in FIG. 1, alternate vacuum shells 80b are mounted on rotatable shafts 81 and are rotatable through 180° about an axis A which is radial with respect to the drum 60, 70. Each of the rotatable shafts 81 is connected, by means of a rack and pinion 82, 83, to a cam follower which runs around a shell turning cam 84. The shell turning cam 84 is shaped so that the rack and pinion 82, 83 operate to rotate the alternate vacuum shells 80b through 180° during a first part of the cycle, prior to transfer of the second web panels, 40b of the incoming web to the receiving web 1, and then return the vacuum shells 80b to their original orientation by rotating them back through minus 180° during a second part of the cycle after the transfer.

In addition, during the first part of the cycle, a shell lifting cam (not shown in FIG. 1 or 2), acts to "lift" the vacuum shell 80b radially outwards from the drum 60, 70. This action helps to apply the second web panels 40b of the incoming web 40 to the receiving web 1 at a transfer step. During the second part of the cycle, after the cut web panels 40b of the incoming web have been transferred to the receiving web 1, the vacuum shells 80b are "withdrawn" radially inwards with respect to the drum 60, 70. During the second part of the cycle, or subsequent to the second part of the cycle, the vacuum shells 80a (i.e. those vacuum shells which have not been rotated during the first part of the cycle) are "lifted" radially outwards from the drum 60, 70. This action helps to apply the first web panels 40a of the incoming web to the receiving web at a transfer step. Finally the vacuum shells 80a are "withdrawn" radially inwards with respect to the drum 60, 70, and the cycle is ready to repeat.

Figure 2:
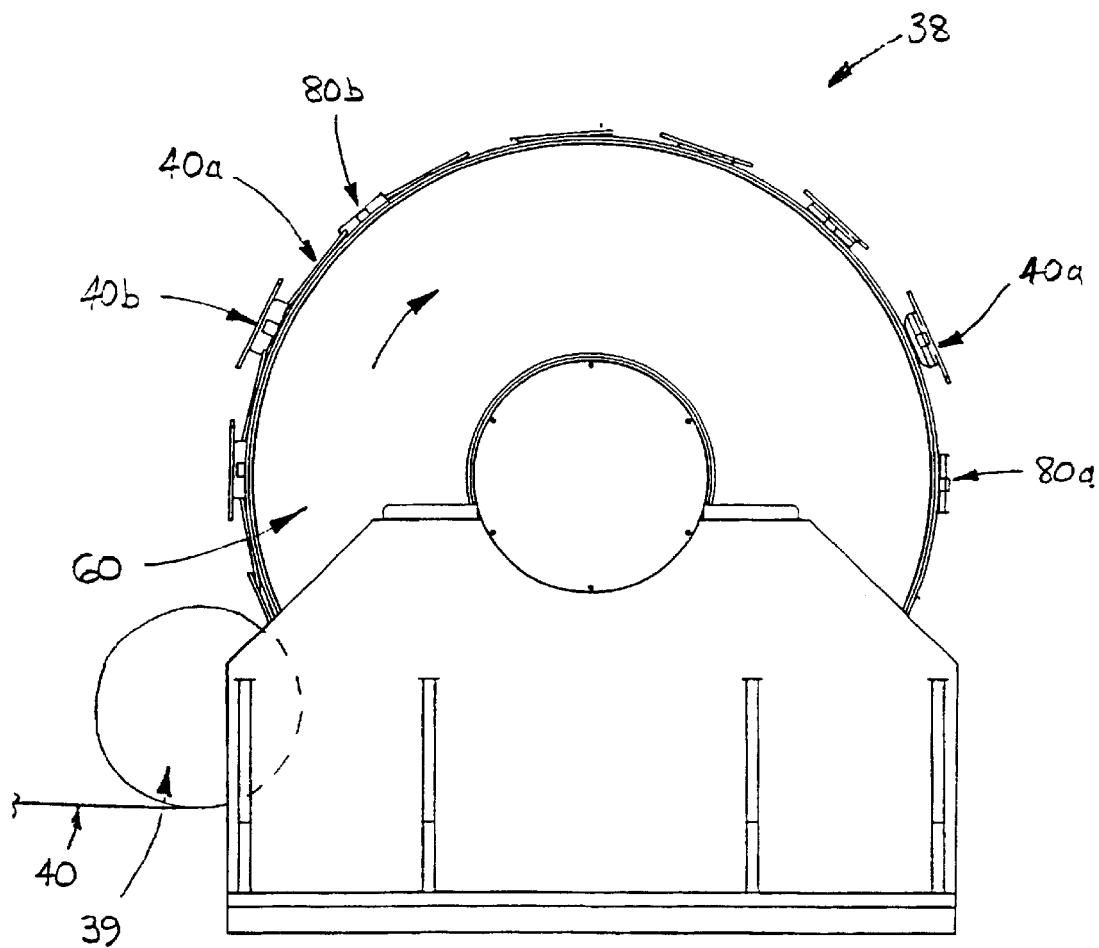
FIG. 2 shows a side elevation view of the apparatus of FIG. 1.

In the embodiment of the invention shown in FIGS. 1 and 2 the second web portion 40b is rotated through 180° in order to provide side panels, and preferably to provide alternately front and rear side panels for an absorbent article such as a diaper. In an alternative embodiment the second web panel 40b is rotated though 90° in order to provide a component in the cross-machine direction, which is perpendicular to the first web panel 40a, preferably wherein the first and second web panels 40a, 40b are elastic. In this alternative embodiment of the invention, the cross-machine direction component may be a waist elastic for an absorbent article such as a diaper. In another alternative embodiment the panels applied during the first part of the cycle of FIG. 1 may be applied directly, without rotation, whilst the alternate panels which are subsequently applied in the second part of the cycle may be rotated (preferably through 180°) prior to application to the receiving web.

Figure 3A:
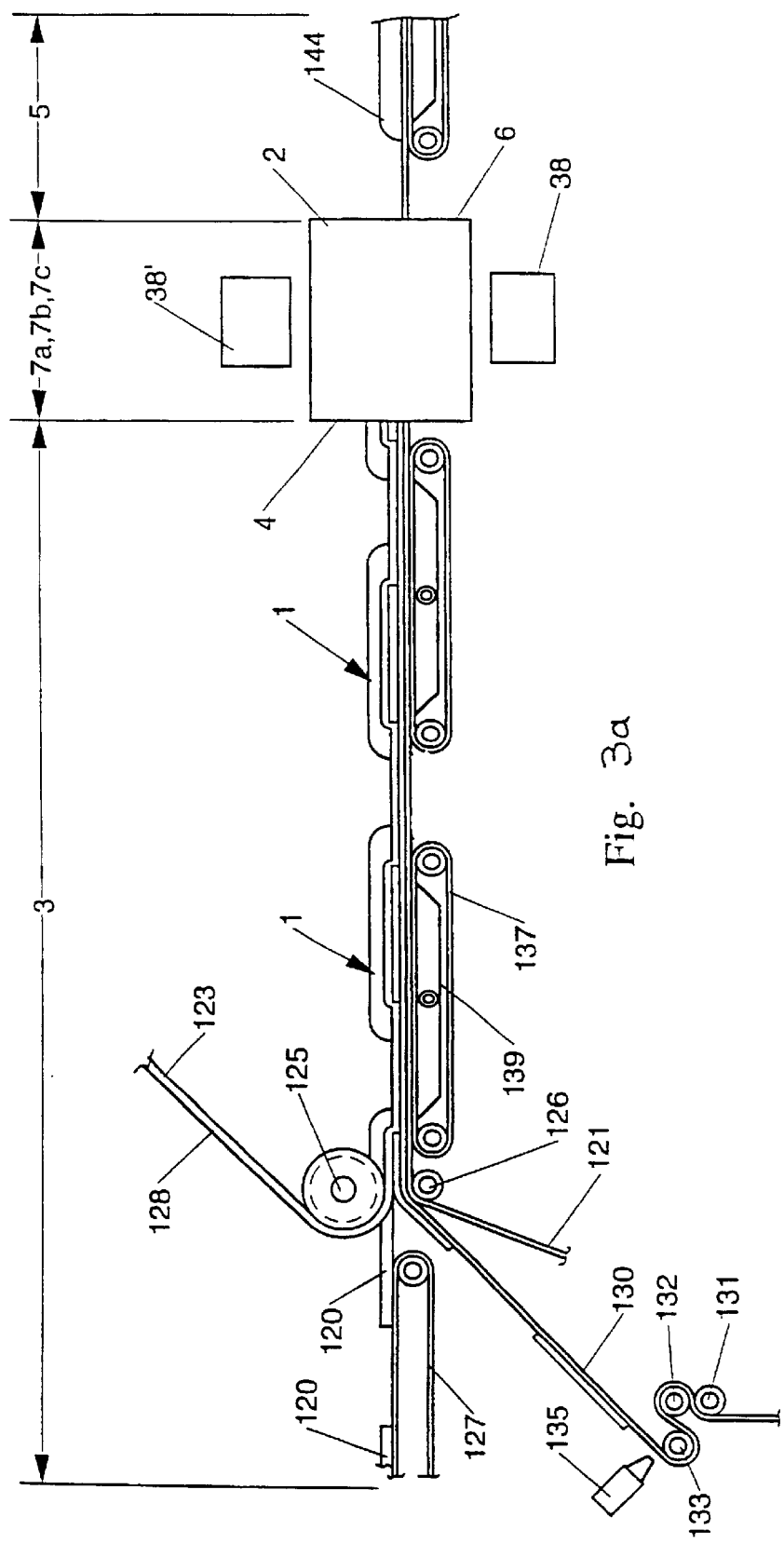
FIG. 3a shows a schematic side elevation view of a production line for the manufacture of an absorbent article.

FIG. 3a shows a side elevation view of a continuous process for making an absorbent article 144. A continuous receiving web 1 is assembled from an absorbent pad element, or core 120, which is encased between a liquid-pervious topsheet 121 and a liquid impervious backsheet 123. The absorbent cores 120 are fed into the nip between a pair of laminating rolls 125, 126 at regularly spaced intervals by means of an infeed conveyor 127. In a preferred embodiment, the cores 120 are comprised of airfelt, within a cellulosic tissue envelope, to provide integrity to the core in use. The backsheet 123 is coated on its inner surface with beads or spirals of adhesive 128, for affixing the backsheet to the core 120. Continuous bands of elastic 130 are fed from metering rolls 131, 132 and 133 past a glue nozzle 135. The S-wrap arrangement of the rolls 131, 132 and 133 minimises deformation of the elastic band 130 and allows for accurate control of the speed of the elastic. The elastic bands are fed into the direction of transport, F, at a lower speed than the cores 120, the backsheet 123 and the topsheet 121, so that the elastic bands 130 are stretched. After passing through the combining nip, the web passes onto a perforated vacuum conveyor belt 137. A vacuum suction box 139 draws the web against the conveyor belt 137, to maintain a uniform tension in the receiving web 1. The web passes at a constant speed of transport to the infeed side 4 of the assembly 2 for periodically changing the speed of web. In the assembly 2, the receiving web 1 can be slowed down, or stopped and is contacted by the apparatus of the invention 38. The apparatus 38 comprises means for providing a web of material such as an elastic side panel, a waist cap or a strip of reinforcement material. The apparatus 38 can be located on the side of the topsheet 121 or on he side of the backsheet 123. The web 1 leaves the outfeed side 6 of the assembly 2 at the constant web speed. The speed of the receiving web portions located upstream and downstream from the assembly 2 along upstream trajectory 3 and downstream trajectory 5 is not affected by the change in speed of those parts of the receiving web 1 that are passing through the assembly 2.

Figure 3B:
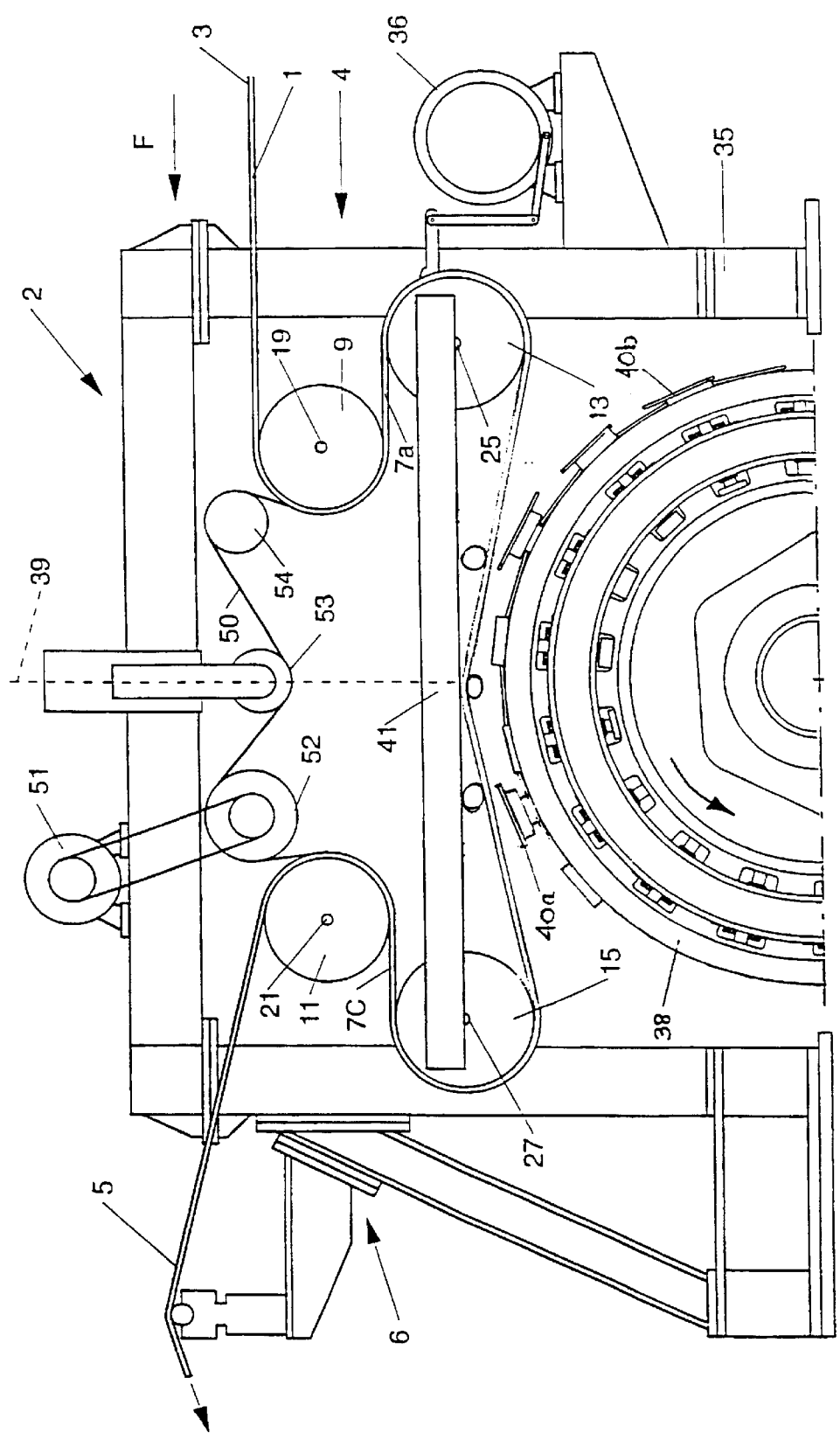
FIG. 3b shows a schematic side elevation view of a part of a production line assembly as shown in FIG. 3a comprising an apparatus of the present invention.

FIG. 3b shows the assembly 2 for changing the speed of a flexible receiving web 1 of relatively low tear strength. By flexible, it is meant that the receiving web 1 can be transported along a curvilinear trajectory and will adapt its shape so as to conform to the trajectory. The receiving web 1 is formed of flexible material, such as paper, airfelt, plastic etc. and can be comprised of the core 120, the topsheet 121, the backsheet 123 or any combination thereof.

The receiving web 1 is transported along the upstream trajectory 3 with a constant velocity of transport $V_0$, in the machine direction F. The upstream trajectory 3 is formed by the length of the receiving web 1 which extends to the right of the first guide roller 9 in FIG. 3b, and which is moving towards the infeed side 4 of the assembly. After passing through the assembly, the receiving web 1 exits at the outfeed side 6 and is transported at constant velocity $V_0$ along the downstream trajectory 5, which extends to the left of the guide roller 11. The upstream and downstream trajectories need not correspond to the machine direction, and can be formed by straight-line or curvilinear paths.

The guide rollers 9 and 11 are rotationally connected to the frame 35. The guide rollers 9, 11 have a fixed position. The receiving web 1 is looped around an upstream and a downstream transport roller 13, 15 which are mounted on a sled 41. The sled 41 is cyclically translated along the frame 35, generally parallel to the machine direction F, by drive motor 36.

An intermediate trajectory 7a, 7b, 7c of the receiving web 1 is located between the upstream guide roller 9 and the downstream guide roller 11, and comprises a first section 7a and a third section 7c, of variable length, located between the upstream guide roller 9 and the upstream transport roller 13 and the downstream transport roller 15 and the downstream guide roller 11 respectively. The second section 7c of the intermediate trajectory 7 is located between the transport rollers 13 and 15 and is of constant length.

Because of the symmetry of the intermediate trajectory 7a, 7b, 7c, the increase in length of the first section 7a, upon displacement of the sled 41 opposite to the machine direction F and away from the equilibrium position 39, is compensated by an equal decrease in length of the third section 7c, and vice versa. As the length of the second section 7b is constant, the whole intermediate trajectory 7a, 7b, 7c is independent of the position of the sled 41 with respect to the frame 35.

When the part of the receiving web that is located along the second section 7b of the intermediate trajectory 7a, 7b, 7c, is stationary (or at least it is slower than the speed of the web speed $V_0$) relative to the frame 35, the web 1 is contacted by the apparatus 38 which is positionally stationary (or at least slower) with respect to the frame 35. After the apparatus 38 has interacted with the receiving web 1, the web is accelerated along the section 7b of the intermediate trajectory towards the outfeed side 6 of the assembly 2, and is supplied to the downstream trajectory 5 with web speed $V_0$.

The guide rollers 9, 11 and the transport rollers 13, 15 are driven by a drive member in the form of a closed loop 50 and pulleys 52, 53 and 54. The loop 50 is partly parallel to the intermediate trajectory 7a, 7b, 7c. The loop 50 is driven at a constant speed which is equal to the speed of transport $V_0$, of the web 1 by a single drive motor 51. By driving the guide rollers 9, 11 and the transport rollers 13, 15, the strain exerted on the web 1 is minimised and can be limited to the acceleration forces, which are acting to change the speed of the web. Further details of suitable assembly are disclosed in EP-A-0 652 175, published on May 10, 1995.

Figure 4:
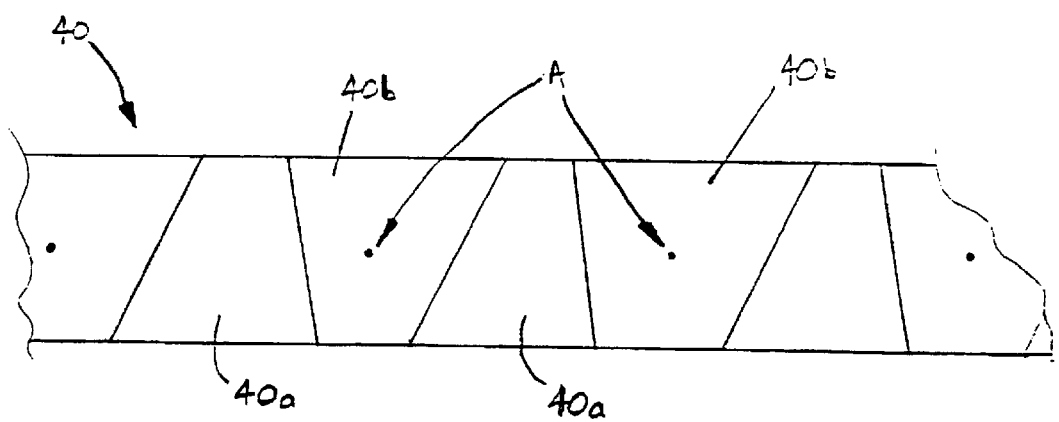
FIG. 4 shows a plan view of web panels after cutting, according to one embodiment of the process of the present invention.

FIG. 4 shows a web 40 which has been cut into discrete portions 40a, 40b. Second we portions 40b are subsequently rotated about their axis A.

The first and second web panels 40a, 40b are applied, and preferably affixed, to the receiving web 1 using any conventional method such as by gluing with adhesives, such as melt adhesives, or use of self-adhesive components, or by use of ultrasonic welding, heat sealing or the like.

What is claimed is:
1. A process for the manufacture of disposable absorbent articles comprising the application of discrete web panels

(40a, 40b) to a receiving web (1), wherein a plurality of first web panels (40a) and second web panels (40b) are cut from the same continuous web (40), and wherein the process comprises the steps of:

cutting the continuous web (40) to form at least a first web panel (40a) and a second web panel (40b);

rotating the second web panel (40b); and applying the first web panel (40a) and the second web panel (40b) to the receiving web (1);

characterised in that the second web panel (40b) is rotated about an axis (A) perpendicular to the plane of the second web panel (40) and wherein the second web panel (40b) is rotated through 180° in order to provide side panels.

2. A process according to claim 1 wherein the second web panel (40b) is rotated though 90° in order to provide a component in the cross-machine direction, which is perpendicular to the first web panel (40a).

3. A process for the manufacture of disposable absorbent articles comprising the application of discrete web panels (40a, 40b) to a receiving web (1), wherein a plurality of first web panels (40a) and second web panels (40b) are cut from the same continuous web (40), and wherein the process comprises the steps of:

cutting the continuous web (40) to form at least a first web panel (40a) and a second web panel (40b);

rotating the second web panel (40b); and applying the first web panel (40a) and the second web panel (40b) to the receiving web (1);

characterised in that the second web panel (40b) is rotated about an axis (A) perpendicular to the plane of the second web panel (40) wherein the first and second web panels (40a, 40b) are applied to the receiving web (1) at substantially matched speeds and wherein the receiving web (1) is fed relative to a stationary frame (35) along an upstream trajectory (3), a downstream trajectory (5), and an intermediate trajectory (7a, 7b, 7b) comprised between the upstream trajectory (3) and the downstream trajectory (5), the web (1) having along the upstream trajectory (3) and along the downstream trajectory (5) a substantially constant speed of transport, wherein the receiving web (1) runs along an upstream and a downstream guide roller (9, 11) that are translationally stationary to the frame (35) and along an upstream and downstream transport roller (13, 15) that are periodically displaced relative to the guide rollers (9, 11) around a transfer position, and wherein the discrete web panels (40a, 40b) are applied to the receiving web (1) when it is at the transfer position.

4. A process according to claim 3 wherein the periodic displacement of the transport rollers (13, 15) around the transfer position occurs at a frequency of between 1 Hz and 100 Hz.

5. A process according to claim 3 wherein the receiving web (1) comprises a liquid-pervious topsheet (121), a liquid impervious backsheet (123), and an absorbent core (120).

6. An apparatus (38) for the manufacture of disposable absorbent articles wherein the apparatus has means for applying discrete web panels (40a, (40b) to a receiving web (1), wherein the apparatus comprises a means for cutting adjacent first web panels (40a) and second web panels (40b) from the same continuous web (40) to form a least the first web panel (40a) and the second web panels (40b);

a means for rotating the second web panel (40b); and a means for applying the first web panel (40a) and the second web panel (40b) to the receiving web (1);

characterised in that the second web panel (40b) is rotated about an axis (A) perpendicular to the plane of the second web panel (40b) and wherein the apparatus (38) further comprises two rotating drums (60, 70) to apply discrete first and second web panels (40a, 40b) to the receiving web (1), and further comprising vacuum shoes (80a, 80b) which are arranged around the circumference of each of the rotating drums (60, 70).

7. An apparatus (38) according to claim 6 wherein at least some of the vacuum shells (80b) are rotatable about an axis (A) perpendicular to the plane of the second web panel (40b).

8. A process for the manufacture of disposable absorbent articles comprising the application of discrete web panels (40a, 40b) to a receiving web (1), wherein a plurality of first web panels (40a) and second web panels (40b) are cut from the same continuous web (40), and wherein the process comprises the steps of:

cutting the continuous web (40) to form at least a first web panel (40a) and a second web panel (40b);

rotating the second web panel (40b); and applying the first web panel (40a) and the second web panel (40b) to the receiving web (1) such that the first web panel (40a) and the second web panel (40b) are spaced apart;

characterised in that the second web panel (40b) is rotated about an axis (A) perpendicular to the plane of the second web panel (40).

9. A process for the manufacture of disposable absorbent articles comprising the application of discrete web panels (40a, 40b) to a receiving web (1), wherein a plurality of first web panels (40a) and second web panels (40b) are cut from the same continuous web (40), and wherein the process comprises the steps of:

cutting the continuous web (40) to form at least a first web panel (40a) and a second web panel (40b);

rotating the second web panel (40b); and applying the first web panel (40a) and the second web panel (40b) to the receiving web (1) such that the first web panel (40a) and the second web panel (40b) are substantially outboard to the receiving web;

characterised in that the second web panel (40b) is rotated about an axis (A) perpendicular to the plane of the second web panel (40).

10. A process according to claim 1 wherein the first web panel (40a) is a front side panel and the second web panel (40b) is a rear side panel.

* * * * *

UNITED STATES PATENT AND TRADEMARK OFFICE
CERTIFICATE OF CORRECTION

PATENT NO. : 6,730,189 B1
DATED : May 4, 2004
INVENTOR(S) : Dirk Franzmann et al.

It is certified that error appears in the above-identified patent and that said Letters Patent is hereby corrected as shown below:

Title page,
Item [57], ABSTRACT,
Line 9, delete "(40)" and insert therefor -- (40b) --.

Column 5,
Line 37, delete "7a, 7b, 7b" and insert therefor -- 7a, 7b, 7c --.

Column 6,
Line 3, delete "a" and insert therefor -- at --.

Signed and Sealed this

Twenty-second Day of March, 2005

JON W. DUDAS
*Director of the United States Patent and Trademark Office*